(12) United States Patent
Kakiuchi et al.

(10) Patent No.: US 9,464,074 B2
(45) Date of Patent: Oct. 11, 2016

(54) METHOD FOR PRODUCING EPOXY COMPOUND

(71) Applicant: NISSAN CHEMICAL INDUSTRIES, LTD., Tokyo (JP)

(72) Inventors: Nobuyuki Kakiuchi, Funabashi (JP); Kazuki Hirasada, Funabashi (JP); Hiroki Yamaguchi, Funabashi (JP); Yutaro Tsuda, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/438,374

(22) PCT Filed: Oct. 21, 2013

(86) PCT No.: PCT/JP2013/078480
§ 371 (c)(1),
(2) Date: Apr. 24, 2015

(87) PCT Pub. No.: WO2014/065239
PCT Pub. Date: May 1, 2014

(65) Prior Publication Data
US 2015/0284372 A1    Oct. 8, 2015

(30) Foreign Application Priority Data

Oct. 25, 2012 (JP) ................. 2012-235374

(51) Int. Cl.
C07D 405/14 (2006.01)
C07D 251/34 (2006.01)
C07D 253/04 (2006.01)

(52) U.S. Cl.
CPC .......... *C07D 405/14* (2013.01); *C07D 251/34* (2013.01); *C07D 253/04* (2013.01)

(58) Field of Classification Search
CPC   C07D 252/34; C07D 405/14; C07D 251/34; C07D 25/34; C07D 405/141
USPC ...................................... 544/221
See application file for complete search history.

(56) References Cited

U.S. PATENT DOCUMENTS

2012/0095225 A1* 4/2012 Yamaura .............. C07D 251/34
544/221

FOREIGN PATENT DOCUMENTS

| | | |
|---|---|---|
| CN | 102603721 A | 7/2012 |
| JP | S59-227872 A | 12/1984 |
| JP | S62-114979 A | 5/1987 |
| JP | H07-206835 A | 8/1995 |
| JP | 2002-145872 A | 5/2002 |
| JP | 2008-239579 A | 10/2008 |
| JP | 2009-256260 A | 11/2009 |
| JP | 2012-025688 A | 2/2012 |
| WO | 2011/093188 A1 | 8/2011 |
| WO | 2012/008308 A1 | 1/2012 |

OTHER PUBLICATIONS

"Shin Jikken Kagaku Koza 14 Yuki Kagobutsu no Gosei to Hanno III," edited by the Chemical Society of Japan, Maruzen Co., Ltd., Feb. 20, 1978, pp. 1342-1353, 1356-1359.
"Jikken Kagaku Koza 20 Yuki Goei II—Alcohol, Amine--", 4th edition, edited by the Chemical Society of Japan, Maruzen Co., Ltd., Jul. 6, 1992, pp. 284-290.
Mu et al., "Synthesis of Triglycidyl Isocyanurate via Oxidation of Triallyl Isocyanurate with Hydrogen Peroxide", STN on the Web, File Caplus, AN=2008: 1203108, Oct. 7, 2008.
Jan. 21, 2014 Search Report issued in International Patent Application No. PCT/JP2013/078480.
Jan. 21, 2014 Written Opinion issued in International Patent Application No. PCT/JP2013/078480.
* cited by examiner

*Primary Examiner* — Venkataraman Balasubramanian
(74) *Attorney, Agent, or Firm* — Oliff PLC

(57) ABSTRACT

There is provided a method for producing an epoxy compound having an epoxy ring bonded to a triazinetrione ring via a long chain alkylene group, an olefin compound having a specific structure is used to efficiently obtain an epoxy compound of which an olefin moiety is epoxidized in high yield. A method for producing an epoxy compound of Formula (2):

Formula (2)

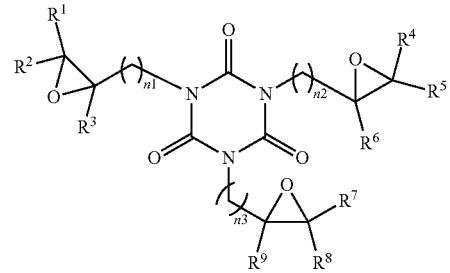

including reacting a triolefin compound of the following Formula (1):

Formula (1)

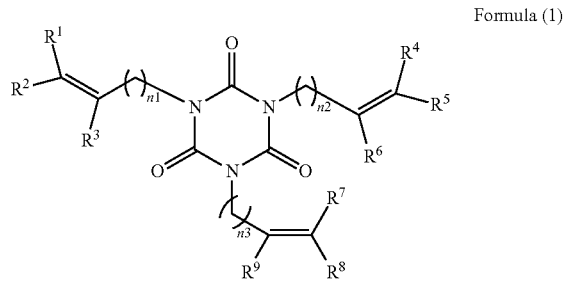

(In the above-mentioned Formulae, $R^1$ to $R^9$ are each independently a hydrogen atom or a methyl group; and n1 to n3 are each independently an integer of 1 to 4) with hydrogen peroxide, a nitrile compound, and an alkaline substance in a solvent. The nitrile compound is an aliphatic nitrile compound or an aromatic nitrile compound. The alkaline substance is phosphate, carbonate, or an alkaline metal hydroxide.

8 Claims, No Drawings

METHOD FOR PRODUCING EPOXY COMPOUND

TECHNICAL FIELD

The present invention relates to a method for producing an epoxy compound from an olefin compound. In addition, the present invention relates to a method for efficiently producing an epoxy compound by a reaction of hydrogen peroxide, a nitrile compound, and an alkaline substance with an olefin compound having a specific structure in a solvent.

BACKGROUND ART

A crystalline epoxy resin generally has a rigid or multifunctional main chain skeleton. Therefore, the crystalline epoxy resin shows high heat resistance and is used in fields in which heat resistance reliability is required, such as electrical and electronic fields.

In some fields, molding such as casting molding is impossible for some applications unless a liquid composition is used, and use of the crystalline epoxy resin is restricted to an application using a solid material such as transfer molding. Therefore, the range of use of the crystalline epoxy resin is restricted.

A traditional epoxy resin used in liquid molding such as casting molding is a liquid epoxy resin, and cannot sufficiently meet a demand for improvement in physical properties of a cured product, such as heat resistance, that is currently demanded more and more in fields of adhesion, casting, sealing, molding, laminating, and the like. Therefore, there is an increasing demand for liquefaction of a crystalline multifunctional epoxy resin that imparts physical properties of a cured product, such as high heat resistance.

Examples of a method for producing such an epoxy compound include a method of epoxidizing an olefin by a reaction of olefin-substituted isocyanurate with hydrogen peroxide as an oxidizer using a mixed catalyst containing tungstate or molybdate as a catalyst, a surfactant (a quaternary ammonium salt used as a phase transfer catalyst), and phosphate or phosphonate (see Patent Document 1).

Additional examples thereof include an epoxidation method in which an olefin compound is reacted with hydrogen peroxide in an aqueous pyrophosphate-pyrophosphoric acid solution in the presence of a nitrile compound (see Patent Document 2). Examples of the olefin compound in this method may include: a $C_{3-15}$ mono-olefin compound such as propylene, 1-butene, t-2-butene, c-2-butene, 1-pentene, isopentene, cyclopentene, 1-hexene, 2-hexene, cyclohexene, norbornene, and 1-octene; a $C_{3-15}$ polyolefin compound such as butadiene, t-1,3-pentadiene, c-1,3-pentadiene, cyclopentadiene, cyclohexadiene, norbornadiene, cyclooctadiene, and vinylcyclohexene; and a polymer having a carbon-carbon double bond in the molecule such as polyester and polyimide.

PRIOR ART DOCUMENTS

Patent Document

Patent Document 1: Japanese Patent Application Publication No. 2012-25688 (JP 2012-25688 A)

Patent Document 2: Japanese Patent Application Publication No. 2002-145872 (JP 2002-145872 A)

SUMMARY OF THE INVENTION

Problem to be Solved by the Invention

In the method of epoxidizing an olefin described in Patent Document 1, it is necessary to remove tungstate or molybdate and a surfactant (a quaternary ammonium salt used as a phase transfer catalyst) that remain in a reaction medium, and an operation of separating a compound of which all three double bonds in the molecule are epoxidized from a compound having a double bond that remains in the molecule is sometimes required from the viewpoint of epoxidation ratio. Thus the method involves a complex a process. Patent Document 2 does not describe a method for efficiently producing an epoxy compound from a specific triolefin compound.

It is an object of the present invention to provide a method for producing an epoxy compound having an epoxy ring bonded to a triazinetrione ring via a long chain alkylene group, which solves such a problem. The inventors of the present invention have found that in a method for producing such an epoxy compound, an olefin compound having a specific structure is used to obtain an epoxy compound of which an olefin moiety is epoxidized with efficiency in high yield. Thus, the present invention has been accomplished.

Means for Solving the Problem

The present invention provides, as a first aspect, a method for producing an epoxy compound of Formula (2):

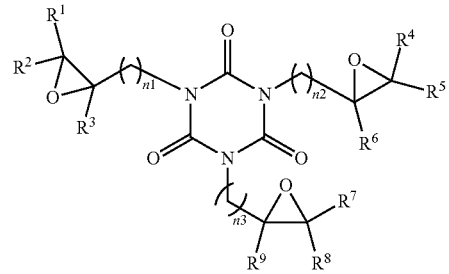

Formula (2)

(In Formula (2), $R^1$ to $R^9$ are each independently a hydrogen atom or a methyl group; and n1 to n3 are each independently an integer of 1 to 4) comprising reacting a triolefin compound of the following Formula (1):

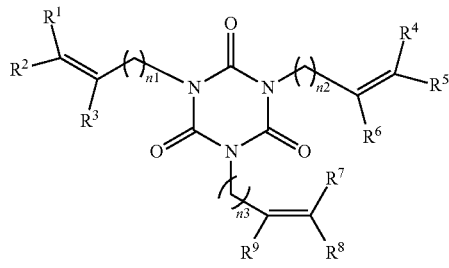

Formula (1)

(In Formula (1), $R^1$ to $R^9$ are each independently a hydrogen atom or a methyl group; and n1 to n3 are each independently an integer of 1 to 4) with hydrogen peroxide, a nitrile compound, and an alkaline substance in a solvent.

The present invention provides, as a second aspect, the method according to the first aspect, in which the nitrile compound is an aliphatic nitrile compound or an aromatic nitrile compound.

The present invention provides, as a third aspect, the method according to the first or second aspect, in which the alkaline substance is phosphate, carbonate, or an alkaline metal hydroxide.

The present invention provides, as a forth aspect, the method according to any one of the first to third aspects, in which the solvent is alcohol.

The present invention provides, as a fifth aspect, the method according to any one of the first to forth aspects, in which the triolefin compound of Formula (1) is obtained by a reaction of cyanuric acid or cyanurate with a $C_{3-9}$ unsaturated alcohol or the unsaturated alcohol having a protected hydroxyl group in a solvent.

The present invention provides, as a sixth aspect, the method according to the fifth aspect, in which a protecting group of the hydroxyl group in the unsaturated alcohol is a sulfonyl group.

The present invention provides, as a seventh aspect, the method according to the fifth aspect, in which a protecting group of the hydroxyl group in the unsaturated alcohol is a p-toluenesulfonyl group, o-nitrobenzenesulfonyl group, or a methanesulfonyl group.

Effect of the Invention

The present invention relates to a novel method for producing an epoxy compound having an epoxy ring bonded to a triazinetrione ring via a long chain alkylene group. An olefin compound bonded to a triazinetrione ring via a long chain alkylene group having a carbon-carbon double bond on or near the terminal is reacted with hydrogen peroxide, a nitrile compound, and an alkaline substance in a solvent to epoxidize the double bond. The inventors have found that when the long chain alkylene group has a specific chain length in this case, the double bond is very efficiently converted into an epoxy group.

Since the olefin compound as an intermediate has high stability, a decrease in the purity due to production of an impurity by cyclization or the like is not caused during the epoxidation.

Further, since a salt of a transition metal oxide and a surfactant (phase transfer catalyst) are not used, it is not necessary to remove them from a product.

Therefore, according to the present invention, an epoxy compound can be efficiently produced with high purity from an olefin compound.

MODES FOR CARRYING OUT THE INVENTION

A triolefin compound used in the present invention is obtained by a reaction of cyanuric acid or cyanurate with an unsaturated alcohol or the unsaturated alcohol having a protected hydroxyl group. In this case, as a protecting group of the unsaturated alcohol having a protected hydroxyl group, a sulfonyl group is used. The inventors have found that an olefin compound as an intermediate can be efficiently obtained using a specific sulfonyl group.

In an epoxy compound obtained by the present invention, a side chain between a triazinetrione ring and an epoxy group substituted on the triazinetrione ring is elongated, intermolecular hydrogen bonds are reduced in terms of properties to hinder stacking of triazine, and as a result, the epoxy compound is liquefied. Completeness of a curing reaction of the epoxy group in the epoxy compound is improved to stabilize a glass transition temperature of a cured product obtained from the epoxy compound. Therefore, the crosslink density is stable even in a heated environment, and toughness can be maintained. Since the curing reaction of the epoxy group is completed in an early stage of curing, the cured product has a stable flexural strength and elastic modulus. Further, water absorption caused by a hydroxyl group produced by hydrolysis of an unreacted epoxy group and a carboxylic acid produced by hydrolysis of a unreacted acid anhydride (curing agent) can be suppressed, and therefore a cured product having a small change in water absorption ratio is obtained.

It is considered that the effects are achieved by involving all the epoxy groups in the reaction, resulting in a cured product having high toughness. This is because the epoxy ring via the long chain alkylene group has a large degree of freedom and high reactivity.

The liquid epoxy compound having a long chain alkylene group can be photo- or heat-cured using a photoacid generator or a thermal acid generator.

A photo-curing material using the liquid epoxy compound of the present invention has characteristics such as fast curing, transparency, and small curing shrinkage, and can be used for coating and adhesion of an electronic part, an optical part, and a precision mechanical part. For example, the photo-curing material can be used for adhesion of an optical element such as a lens of a cell phone or a camera, a light-emitting diode (LED), and a semiconductor laser (LD), a part such as a liquid crystal panel, a biochip, and a lens and a prism of a camera, a magnetic part of a hard disc of a personal computer, and the like, a pickup (a part capturing optical information reflected from a disc) of a CD or DVD player, a cone and a coil of a speaker, a magnet of a motor, a circuit substrate, an electronic part, and a part inside an engine of an automobile, and the like.

The epoxy compound of the present invention can be applied to a hard coating material for surface protection of an automobile body, a lamp, an electrical appliance, a construction material, a plastic, and the like. For example, the epoxy compound can be applied to bodies of an automobile and a motorbike, a lens and a mirror of a head light, a plastic lens of glasses, a cell phone, a game machine, an optical film, and an ID card.

Further, the epoxy compound of the present invention can be applied to an ink material to be printed on a metal such as aluminum, a plastic, and the like. For example, the epoxy compound can be applied to an ink to be printed on a card such as a credit card and a membership card, a switch and a keyboard of an electrical appliance and office automation equipment, and an ink for an inkjet printer for CD, DVD.

In addition, the epoxy compound of the present invention can be applied to a technique for forming a complicated solid object by curing a resin in combination with three-dimensional CAD, optical shaping such as modeling of an industrial product, coating of optical fibers, adhesion, optical waveguide, thick film resist (for MEMS), and the like.

Specifically, the present invention provides a method for producing an epoxy compound of Formula (2) comprising reacting a triolefin compound of Formula (1) with hydrogen peroxide, a nitrile compound, and an alkaline substance in a solvent.

In Formula (1), $R^1$ to $R^9$ are each independently a hydrogen atom or a methyl group, and n1 to n3 are each independently an integer of 1 to 4.

In Formula (2), $R^1$ to $R^9$ are each independently a hydrogen atom or a methyl group, and n1 to n3 are each independently an integer of 1 to 4.

$R^1$ to $R^8$ are each independently a hydrogen atom or a methyl group, but a hydrogen atom is preferably used. When a side chain extending from an isocyanurate ring (triazinetrione ring) has a total carbon atom number of 3 to 9, a $C_{2-6}$ alkyl group as described below can be used in place of a hydrogen atom and a methyl group.

Examples of the $C_{2-6}$ alkyl group include an ethyl group, a n-propyl group, an i-propyl group, a cyclopropyl group, a n-butyl group, an i-butyl group, a s-butyl group, a tert-butyl group, a cyclobutyl group, a 1-methyl-cyclopropyl group, a 2-methyl-cyclopropyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

A triazinetrione ring is bonded to an epoxy group via an alkylene group in which n1 to n3 are each independently an integer of 1 to 4.

The amount of hydrogen peroxide to be used during production of the epoxy compound from the triolefin compound is 0.5 to 50 equivalents, 0.5 to 30 equivalents, or 1 to 10 equivalents, relative to 1 equivalent of double bond in the triolefin compound. Hydrogen peroxide is added to a reaction system, for example, in a form of 35% by mass of aqueous hydrogen peroxide. Hydrogen peroxide may be all added once. Alternatively, a method of sequentially adding a predetermined amount of hydrogen peroxide in several portions (e.g., in about 2 to 5 portions) may be used. In the addition of aqueous hydrogen peroxide, a dropping method is applied, and one portion of aqueous hydrogen peroxide is dropped over 1 to 2 hours. After that, a reaction can be carried out for 1 to 2 hours.

The combination of the addition (dropping) and subsequent reaction (dropping and reaction) is repeated several times (e.g., about 2 to 5 times), thereby the yield in the reaction to obtain the epoxy group from the olefin can be improved.

Examples of the nitrile compound used during production of the epoxy compound from the triolefin compound include an aliphatic nitrile compound and aromatic nitrile. Examples of the aromatic nitrile include benzonitrile, and examples of the aliphatic nitrile include acrylonitrile and propionitrile. In particular, the aliphatic nitrile is preferred, and acetonitrile is preferably used. The amount of nitrite compound to be used is 0.5 to 50 equivalents, 1 to 30 equivalents, or 3 to 10 equivalents, relative to 1 equivalent of double bond in the olefin compound.

Examples of the alkaline substance used during production of the epoxy compound from the triolefin compound of the present invention include a phosphoric acid-based compound, a carbonate-based compound, and an alkaline metal hydroxide. Specific examples of the phosphoric acid-based compound include phosphoric acid, pyrophosphoric acid, polyphosphoric acid, and salts thereof. Examples of the carbonate-based compound include sodium carbonate, potassium carbonate, ammonium carbonate, sodium hydrogen carbonate, potassium hydrogen carbonate, and ammonium hydrogen carbonate. Examples of the alkaline metal hydroxide include sodium hydroxide and potassium hydroxide. In particular, phosphate, carbonate, and alkaline metal hydroxide are preferred. As phosphate, sodium phosphate, potassium phosphate, ammonium phosphate, or the like is used. As carbonate, sodium carbonate, sodium hydrogen carbonate, or the like is used. As alkaline metal hydroxide, sodium hydroxide is used. The amount of alkaline substance to be added is 0.01 to 10 equivalents, or 0.01 to 2 equivalents, relative to 1 equivalent of double bond in the olefin compound.

In the reaction, a buffer solution may be added. Examples of the buffer solution include a sodium carbonate-sodium hydrogen carbonate buffer solution (pH: 9.2 to 10.6). For example, the pH can be adjusted to a predetermined pH by mixing an aqueous 0.1 mol/L sodium carbonate solution and an aqueous 0.1 mol/L sodium hydrogen carbonate solution.

As the solvent used in the reaction to obtain the epoxy compound from the triolefin compound, an alcoholic solvent is used. As the alcoholic solvent, a linear, branched, or cyclic alcohol such as methanol, ethanol, isopropanol, n-butanol, t-amyl alcohol, and cyclohexanol is used. In particular, methanol is preferably used. A non-alcoholic solvent such as toluene may be mixed in the alcoholic solvent.

The reaction to obtain the epoxy compound from the triolefin compound can be carried out at 5 to 60° C. for 5 to 20 hours.

If necessary, a solution after the reaction is filtered to remove an inorganic salt, water is added, and the solvent and the nitrile compound are removed by distillation under reduced pressure to obtain an aqueous phase. An organic phase is obtained by extraction with chloroform or the like from the aqueous phase. The organic phase is washed with an aqueous 1 to 5% by mass sodium thiosulfate solution, an aqueous acid solution (e.g., aqueous 0.1 to 2 N phosphoric acid solution), and pure water by turns, and dried. Thus, a product can be obtained.

A conversion ratio of the olefin into an epoxy group is 60% or more, for example, 75% or more, or 90% or more.

Examples of the epoxy compound obtained from the triolefin compound include as follows.

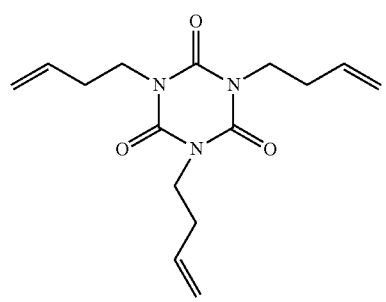
Formula (A-1)
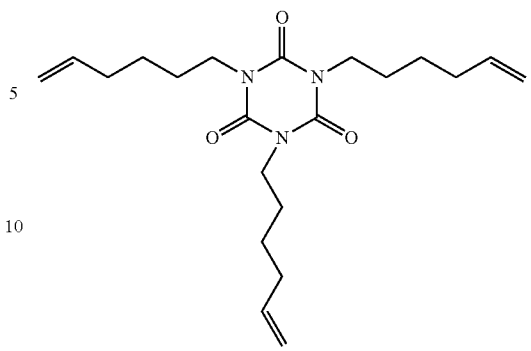
Formula (A-3)
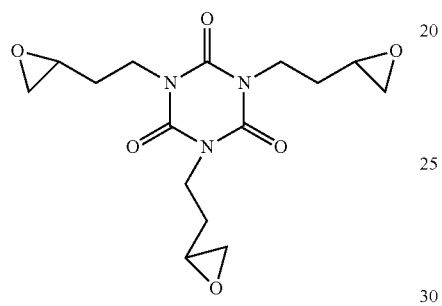
Formula (B-1)
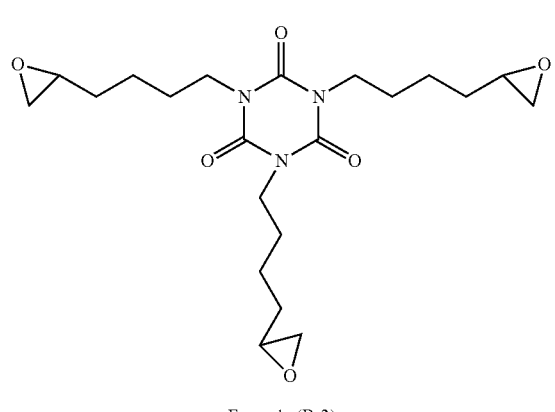
Formula (B-3)
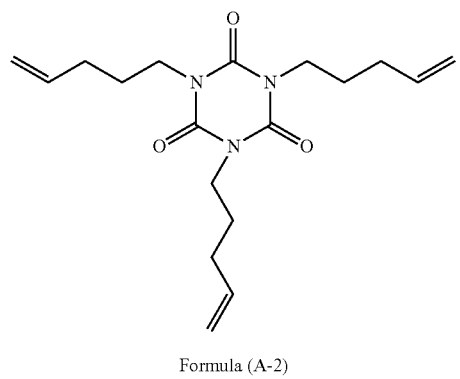
Formula (A-2)
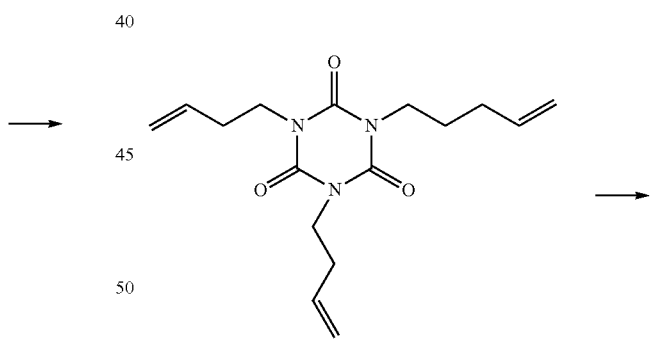
Formula (A-4)
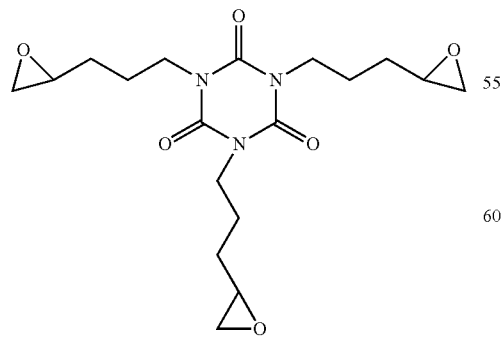
Formula (B-2)
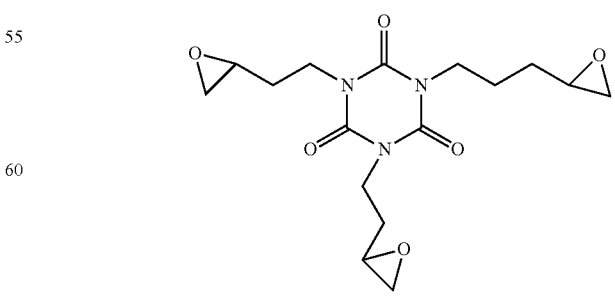
Formula (B-4)

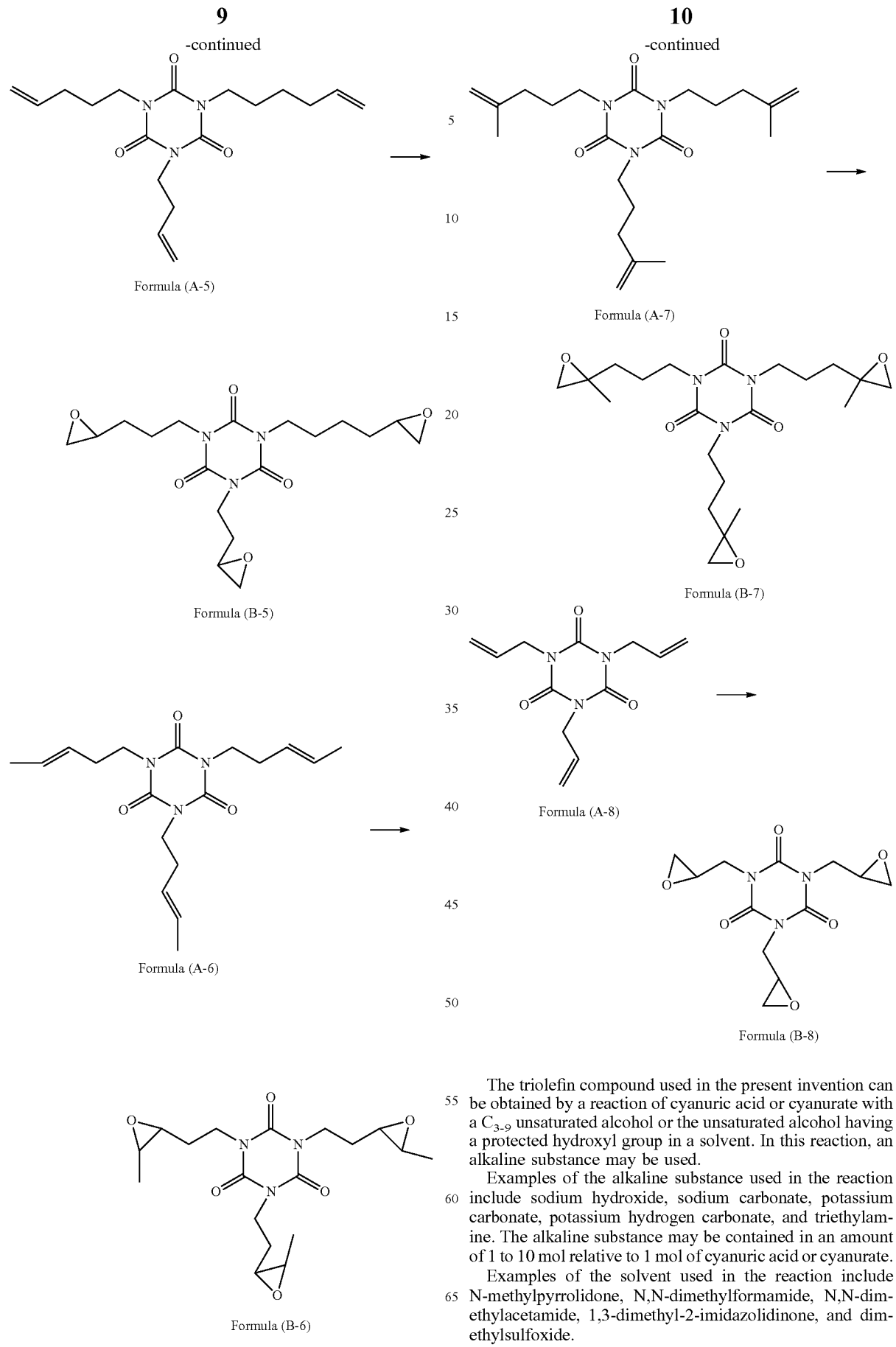

The triolefin compound used in the present invention can be obtained by a reaction of cyanuric acid or cyanurate with a $C_{3-9}$ unsaturated alcohol or the unsaturated alcohol having a protected hydroxyl group in a solvent. In this reaction, an alkaline substance may be used.

Examples of the alkaline substance used in the reaction include sodium hydroxide, sodium carbonate, potassium carbonate, potassium hydrogen carbonate, and triethylamine. The alkaline substance may be contained in an amount of 1 to 10 mol relative to 1 mol of cyanuric acid or cyanurate.

Examples of the solvent used in the reaction include N-methylpyrrolidone, N,N-dimethylformamide, N,N-dimethylacetamide, 1,3-dimethyl-2-imidazolidinone, and dimethylsulfoxide.

Examples of the cyanurate include trisodium cyanurate and tripotassium cyanurate that are derived from cyanuric acid.

In the reaction, cyanuric acid or cyanurate can be reacted with a $C_{3-9}$ unsaturated alcohol or the unsaturated alcohol having a protected hydroxyl group, for example, in an amount of 0.3 to 9 mol or 0.3 to 27 mol relative to 1 mol of cyanuric acid or cyanurate. Further, an excess amount of the unsaturated alcohol or the unsaturated alcohol having a protected hydroxyl group may be used.

In order to involve a proper amount of relatively expensive unsaturated alcohol or the unsaturated alcohol having a protected hydroxyl group in the reaction to selectively obtain a tris compound, focus is placed on a range deviating from the equivalent weight ratio and the unsaturated alcohol or the unsaturated alcohol having a protected hydroxyl group can be subjected to the reaction a focus on.

Specifically, in the reaction, cyanuric acid or cyanurate can be reacted with a $C_{3-9}$ unsaturated alcohol or the unsaturated alcohol having a protected hydroxyl group, for example, in an amount of 0.3 to 5 mol relative to 1 mol of cyanuric acid or cyanurate.

For example, 1 mol of cyanuric acid can be reacted with 1 to 5 mol or 2 to 5 mol of $C_{3-9}$ unsaturated alcohol or the unsaturated alcohol having a protected hydroxyl group. One mol of cyanurate can be reacted with 0.3 to 1 mol or 0.3 to 2 mol of $C_{3-9}$ unsaturated alcohol or the unsaturated alcohol having a protected hydroxyl group.

Therefore, when cyanurate is used, a tris compound can be selectively produced using a relatively expensive unsaturated alcohol in an amount that is equal to or less than the equivalent weight ratio.

This is considered as follows. Cyanuric acid and cyanurate have low solubility to the solvent. In particular, cyanurate has lower solubility to the solvent than cyanuric acid. For example, in a reaction of 1 mol of cyanurate (having three N—Na groups in the molecule) with 1 mol of unsaturated alcohol or the unsaturated alcohol having a protected hydroxyl group, one of the N—Na groups in one molecule of cyanuric acid is first reacted with the unsaturated alcohol or the unsaturated alcohol having a protected hydroxyl group during a reaction process, to produce an intermediate in which cyanuric acid has a substituted alkenyl group. Therefore, it is considered that the solubility of the molecule (intermediate) to the solvent is improved. The intermediate having the improved solubility to the solvent has enhanced reactivity as compared with another cyanurate (unsubstituted), and the intermediate may further be subjected to substitution with an alkenyl group and another alkenyl group to synthesize triolefin isocyanurate. This pattern is caused even in a case of cyanuric acid, but it is considered that the reaction of cyanurate having lower solubility markedly proceeds as compared with cyanuric acid.

As an additive in the reaction, halogenated metal such as potassium bromide and potassium iodide can be used. The halogenated metal can be used in an amount of 0.01 to 1 mol relative to 1 mol of isocyanuric acid. In particular, in a reaction of isocyanuric acid with an unsaturated alcohol or the unsaturated alcohol having a protected hydroxyl group, the additive is preferably added.

The reaction can be carried out at 20 to 100° C. for 1 to 20 hours.

Examples of the unsaturated alcohol or the unsaturatead alcohol having a protected hydroxyl group for synthesis of the triolefin compound include a $C_{3-9}$ unsaturated alcohol or the unsaturatead alcohol having a protected hydroxyl group.

The carbon atom number of 3 to 9 represents a carbon atom number of unsaturated hydrocarbon group excluding a protecting group.

Examples of the protecting groups include a p-toluenesulfonyl group, an o-nitrobenzenesulfonyl group, and a methanesulfonyl group. A p-toluenesulfonyl group and a methanesulfonyl group are preferred. In particular, a methanesulfonyl is preferably used since the yield of olefin compound to be obtained is high.

The unsaturated alcohol or the unsaturated alcohol having a protected hydroxyl group is linear or branched unsaturated alcohol shown below. In the following formulae, $X^1$ is a hydrogen atom, a p-toluenesulfonyl group, an o-nitrobenzenesulfonyl group, or a methanesulfonyl group.

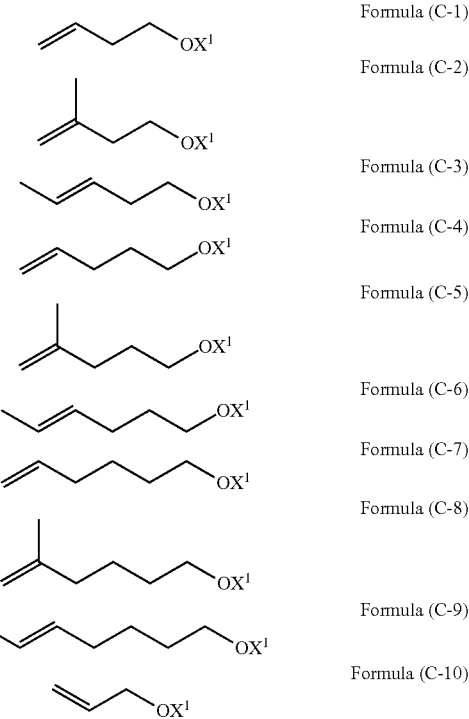

Formula (C-1)
Formula (C-2)
Formula (C-3)
Formula (C-4)
Formula (C-5)
Formula (C-6)
Formula (C-7)
Formula (C-8)
Formula (C-9)
Formula (C-10)

The unsaturated alcohol having the protected hydroxyl group is obtained by a reaction of $C_{3-9}$ unsaturated alcohol with p-toluenesulfonyl halide, o-nitrobenzensulfonyl halide, or methanesulfonyl halide in the presence of an alkaline substance in a solvent. As the halide, a halide such as fluoride, chloride, bromide, and iodide is used.

Examples of the alkaline substance used in the reaction include sodium hydroxide, sodium carbonate, potassium carbonate, potassium hydrogen carbonate, and triethylamine.

Examples of the solvent used in the reaction include N-methylpyrrolidone, N,N-dimethylformamide, N,N-dimethylacetamide, 1,3-dimethyl-2-imidazolidinone, dimethylsulfoxide, and toluene.

The reaction of cyanuric acid or cyanurate with the $C_{3-9}$ unsaturated alcohol or the unsaturated alcohol having a protected hydroxyl group is shown below. In the following formulae, $X^1$ is a hydrogen atom, a p-toluenesulfonyl group, an o-nitrobenzenesulfonyl group, or a methanesulfonyl group, and $X^2$ is a hydrogen atom, sodium, or potassium.

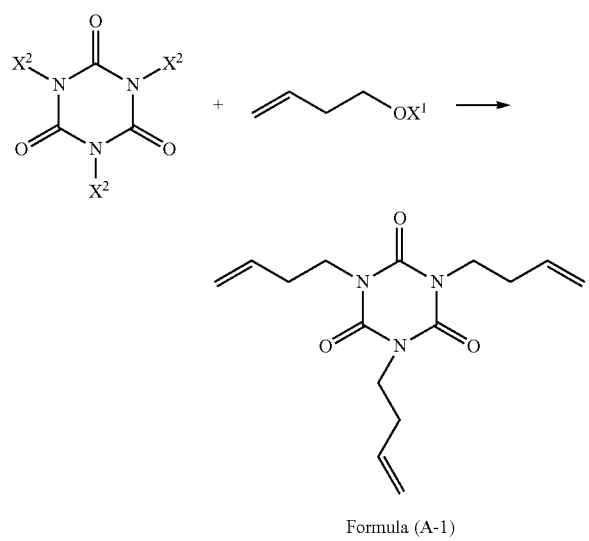
Formula (A-1)
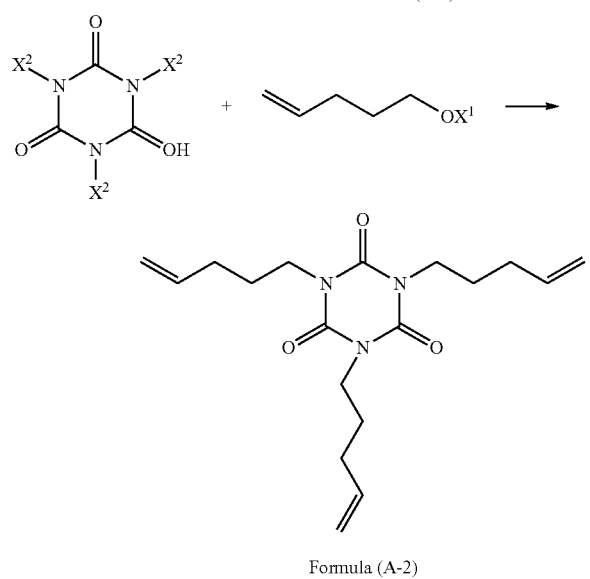
Formula (A-2)
Formula (A-3)
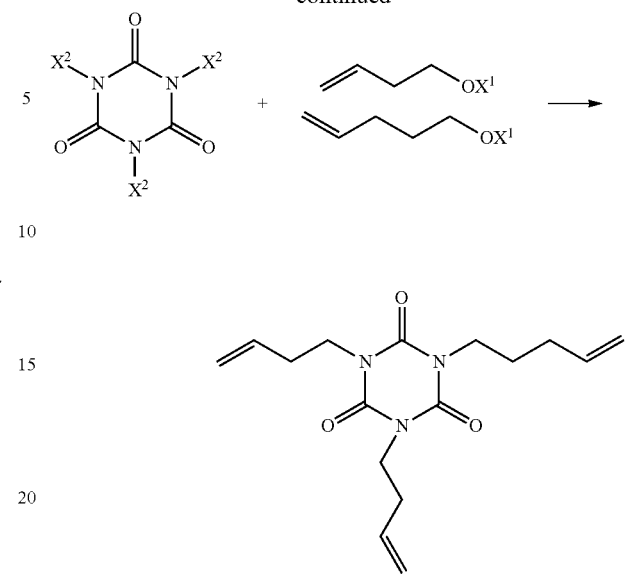
Formula (A-4)
Formula (A-5)
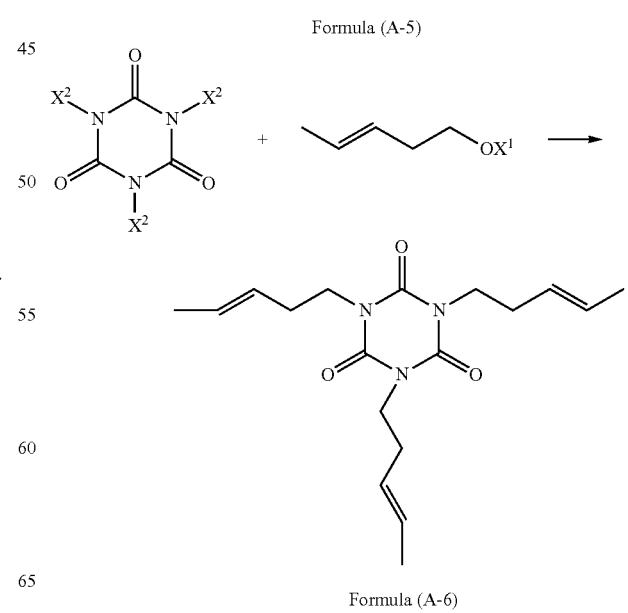
Formula (A-6)

-continued

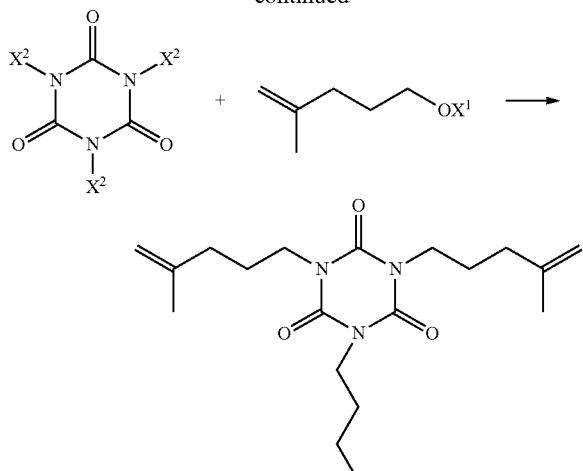

Formula (A-7)

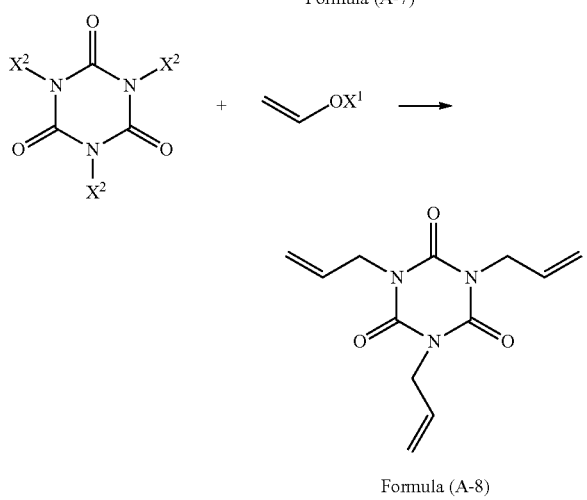

Formula (A-8)

EXAMPLES

Hereinafter, the present invention will be described in more detail by Examples, and the present invention is not limited to these Examples.

In Examples, devices used for analysis of samples are as follows.

HPLC (high performance liquid chromatography)

Device: 1200 Series manufactured by Agilent Technologies

GC (gas chromatography)

Device: 7890A manufactured by Agilent Technologies

Synthesis Example 1

Trisodium isocyanurate (5.3 g, 27.0 mmol), 4-pentenyl methanesulfonate (4.4 g, 27.0 mmol), and dimethyl sulfoxide (44.4 g) were mixed and the mixture was heated to 65° C. to cause a reaction for 19 hours. The reaction solution was analyzed by HPLC, and the yield of 1,3,5-tris-(4-pentenyl)-isocyanurate was confirmed to be 91%.

Synthesis Example 2

Isocyanuric acid (45 mg, 0.35 mmol), sodium carbonate (106 mg, 1 mmol), potassium bromide (12 mg, 0.1 mmol), and dimethyl sulfoxide (1.6 g) were mixed and the mixture was heated to 100° C., and stirred for 1 hour. The reaction solution was cooled to 65° C., and a mixed solution of 4-pentenyl methanesulfonate (164 mg, 1 mmol), and dimethyl sulfoxide (164 mg) was added dropwise over 1 hour. A reaction was carried out for 16 hours. The reaction solution was analyzed by HPLC, and the yield of 1,3,5-tris-(4-pentenyl)-isocyanurate was confirmed to be 77%.

Synthesis Example 3

Isocyanuric acid (135 mg, 1.1 mmol), sodium carbonate (318 mg, 3.0 mmol), potassium bromide (36 mg, 0.3 mmol), and dimethyl sulfoxide (4.1 g) were mixed, and the mixture was heated to 65° C. A mixed solution of 2-propenyl methanesulfonate (409 mg, 3.0 mmol) and dimethyl sulfoxide (409 mg) was added dropwise over 30 minutes. A reaction was carried out for 1 hour. The reaction solution was analyzed by GC, and the yield of 1,3,5-tris-(2-propenyl)-isocyanurate was confirmed to be 68%.

Comparative Synthesis Example 1

Isocyanuric acid (4.8 g, 37.5 mmol), triethylamine (11.4 g, 112.6 mmol), and N-methyl pyrrolidone (75.0 g) were mixed, and the mixture was heated to 90° C. 11-Bromoundecene (25.0 g, 107.2 mmol) was added dropwise over 1 hour. A reaction was carried out for 3 hours, the reaction solution was filtered, a mixed solvent of heptane (100.0 g) and 5% by mass of salt solution (75.0 g) was added, and the mixture was separated into an aqueous phase and an organic phase.

An organic phase was obtained by extraction with heptane (100.0 g) from the aqueous phase, combined with the separated organic phase, and the mixture was washed twice with 5% by mass of salt solution (75.0 g). The solvent of the resulting organic phase was distilled off under reduced pressure and the organic phase was completely concentrated. The yield of 1,3,5-tris-(10-undecenyl)-isocyanurate was confirmed to be 65%.

Example 1

1,3,5-tris-(4-pentenyl)-isocyanurate (3.0 g, 9.0 mmol), trisodium phosphate dodecahydrate (7.2 g, 18.9 mmol), acetonitrile (10 g, 243.0 mmol), methanol (6 g), and sodium carbonate-sodium hydrogen carbonate buffer solution (pH=10.6) (10 g) were mixed, the temperature was adjusted to 20° C., and an aqueous 35% by mass hydrogen peroxide solution (2.32 mL, 27 mmol) was added dropwise over 1 hour to cause a reaction for 2 hours. Further, the operation of adding dropwise an aqueous 35% by mass hydrogen peroxide solution (2.32 mL, 27 mmol) over 1 hour to cause a reaction for 2 hours was repeated three times, and then the reaction was carried out for additional 4 hours. The reaction solution was analyzed by GC, and the conversion ratio of olefin was 99%.

The reaction mixture was filtered to remove an inorganic salt, the reaction solution was analyzed by HPLC, and the yield of 1,3,5-tris-(4,5-epoxypentyl)-isocyanurate was confirmed to be 94%.

Example 2

1,3,5-tris-(2-propenyl)-isocyanurate (2.2 g, 9.0 mmol), trisodium phosphate dodecahydrate (7.2 g, 18.9 mmol), acetonitrile (10 g, 243.0 mmol), methanol (6 g), and sodium carbonate-sodium hydrogen carbonate buffer solution (pH=10.6) (10 g) were mixed, the temperature was adjusted to 20° C., and an aqueous 35% by mass hydrogen peroxide solution (2.32 mL, 27 mmol) was added dropwise over 1 hour to cause a reaction for 2 hours. Further, the operation of adding dropwise an aqueous 35% by mass hydrogen peroxide solution (2.32 mL, 27 mmol) to cause a reaction for 2 hours was repeated four times, and then the reaction was carried out for additional 4 hours. The reaction solution was analyzed by GC, and the conversion ratio of olefin was 99%.

Water was added to the reaction mixture to make it uniform, and methanol and acetonitrile were distilled off under reduced pressure. To the remained aqueous phase, chloroform (50 g) was added, and the mixture was separated into an organic phase and an aqueous phase. An organic phase was obtained by extraction with chloroform (50 g) from the aqueous phase. The organic phase was combined with the obtained organic phase, washed with an aqueous 2% sodium thiosulfate solution (50 g), an aqueous 1 N phosphoric acid solution (50 g), and ion-exchanged water (50 g) twice, and dried under reduced pressure by a vacuum pump. As a result, 1,3,5-tris-(2,3-epoxypropyl)-isocyanurate was obtained in an amount of 0.8 g, a yield of 28%, and a GC area percent purity of 90%.

Example 3

1,3,5-Tris-(4-pentenyl)-isocyanurate (10.0 g, 30.0 mmol), acetonitrile (11 g, 270.0 mmol), and methanol (30 g) were mixed, and the temperature was adjusted to 25° C. An aqueous 35% by mass hydrogen peroxide solution (23.2 mL, 270.0 mmol) was added dropwise over 15 hours. At the same time as onset of the dropwise addition of aqueous 35% by mass hydrogen peroxide solution, an aqueous 8% by mass sodium hydroxide solution was started to be added dropwise so that the pH of the reaction solution was maintained at 10.0 to 10.5. The reaction solution was analyzed by GC, and the conversion ratio of olefin was 99%.

The resultant solution was analyzed by HPLC, and the yield of 1,3,5-tris-(4,5-epoxypentyl)-isocyanurate was confirmed to be 71%.

Example 4

1,3,5-Tris-(4-pentenyl)-isocyanurate (10.0 g, 30.0 mmol), trisodium phosphate dodecahydrate (23.9 g, 63.0 mmol), acetonitrile (11 g, 270.0 mmol), and methanol (30 g) were mixed, the temperature was adjusted to 20° C., and an aqueous 35% by mass hydrogen peroxide solution (7.74 mL, 90 mmol) was added dropwise over 1 hour to cause a reaction for 4 hours. Further, the operation of adding dropwise an aqueous 35% by mass hydrogen peroxide solution (7.74 mL, 90 mmol) over 1 hour to cause a reaction for 4 hours was repeated twice, and the reaction was carried out for additional 4 hours. The reaction solution was analyzed by GC, and the conversion ratio of olefin was 99%.

The reaction mixture was filtered to remove an inorganic salt, the reaction solution was analyzed by HPLC, and the yield of 1,3,5-tris-(4,5-epoxypentyl)-isocyanurate was confirmed to be 75%.

Comparative Example 1

1,3,5-Tris-(10-undecenyl)-isocyanurate (5.3 g, 9.0 mmol), trisodium phosphate dodecahydrate (7.2 g, 18.9 mmol), acetonitrile (10 g, 243.0 mmol), methanol (6 g), and sodium carbonate-sodium hydrogen carbonate buffer solution (pH=10.6) (10 g) were mixed, the temperature was adjusted to 20° C., and an aqueous 35% by mass hydrogen peroxide solution (2.32 mL, 27 mmol) was added dropwise over 1 hour to cause a reaction for 2 hours. Further, the operation of adding dropwise an aqueous 35% by mass hydrogen peroxide solution (2.32 mL, 27 mmol) over 1 hour to cause a reaction for 2 hours was repeated three times, and the reaction was carried out for additional 4 hours. The reaction solution was analyzed by GC, and the conversion ratio of olefin was 0%.

INDUSTRIAL APPLICABILITY

In a method for producing an epoxy compound having an epoxy ring bonded to a triazinetrione ring via a long chain alkylene group, an olefin compound having a specific structure is used to efficiently obtain an epoxy compound of which an olefin moiety is epoxidized in high yield.

The invention claimed is:
1. A method for producing an epoxy compound of Formula (2):

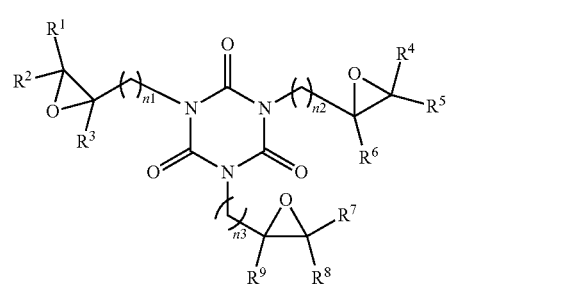

Formula (2)

wherein $R^1$ to $R^9$ are each independently a hydrogen atom or a methyl group;
and n1 to n3 are each independently an integer of 2 to 4, comprising reacting a triolefin compound of the following Formula (1):

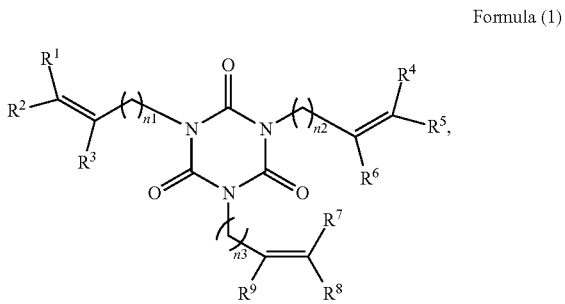

Formula (1)

wherein $R^1$ to $R^9$ are each independently a hydrogen atom or a methyl group;
and n1 to n3 are each independently an integer of to 2 to 4, with hydrogen peroxide, a nitrile compound, and an alkaline substance in a solvent including a buffer solution.
2. The method according to claim 1, wherein the nitrile compound is an aliphatic nitrile compound or an aromatic nitrile compound.

3. The method according to claim 1, wherein the alkaline substance is phosphate, carbonate, or an alkaline metal hydroxide.

4. The method according to claim 1, wherein the solvent is alcohol.

5. The method according to claim 1, wherein the triolefin compound of Formula (1) is obtained by a reaction of cyanuric acid or cyanurate with a $C_{3-9}$ unsaturated alcohol having a protected hydroxyl group in the solvent, wherein the protected hydroxyl group is a leaving group.

6. The method according to claim 5, wherein a protecting group of the hydroxyl group in the unsaturated alcohol is a sulfonyl group.

7. The method according to claim 5, wherein a protecting group of the hydroxyl group in the unsaturated alcohol is a p-toluenesulfonyl group, o-nitrobenzenesulfonyl group, or a methanesulfonyl group.

8. The method according to claim 1, further comprising reacting a cyanuric acid or cyanurate with a $C_{3-9}$ unsaturated alcohol having a protected hydroxyl group in the solvent, wherein the protected hydroxyl group is a leaving group, to obtain the triolefin compound of Formula (1).

* * * * *